United States Patent [19]

Higgins

[11] Patent Number: 4,473,643
[45] Date of Patent: Sep. 25, 1984

[54] MICROBIOLOGICAL OXIDATION PROCESS

[75] Inventor: Irving J. Higgins, Wilden, England

[73] Assignee: Imperial Chemical Industries PLC, London, England

[21] Appl. No.: 364,459

[22] Filed: Apr. 1, 1982

[30] Foreign Application Priority Data

Apr. 2, 1981 [GB] United Kingdom ................. 8110320

[51] Int. Cl.$^3$ ............................................. C12P 7/02
[52] U.S. Cl. .................................... 435/157; 435/155
[58] Field of Search ........................ 435/161, 155, 157

[56] References Cited

FOREIGN PATENT DOCUMENTS 45-84057 9/1970 Japan.

OTHER PUBLICATIONS

Chemical Abstracts, vol. 92, No. 25, Jun. 23, 1980, p. 471, No. 213540n, Columbus, Ohio, U.S.A. & JP—A—80 0065 (Mitsui Petrochemical Industries, Ltd.), 5-1-1980, *Abstract*.
Chemical Abstracts, vol. 80, No. 9, Mar. 4, 1974, pp. 162, 163, No. 45517s, Columbus, Ohio, U.S.A., H. Aurich et al: "Oxidation of n-hexadecane by *Acinetobacter-calco-aceticus*. Restriction and Induction of the Participating Enzyme", and Z. Allg. Mikrobiol., 1973, 13(7), 539–544, *Abstract and Full Text*.
Chemical Abstracts, vol. 87, No. 19, Nov. 7, 1977, p. 277, No. 148444q, Columbus, Ohio, U.S.A., O. Asperger et al.: "Use of Polarographic Oxygen Measurements in the Respiratory Consumption of n-alkanes and Their Derivatives by *Acinetobacter calcoaceticus*", and Z. Allg. Mikrobiol., 1977, 17(6), 419–427, *Abstract and Full Text*.
Chemical Abstracts, vol. 86, No. 19, May 9, 1977, p. 257, No. 136091p, Columbus, Ohio, U.S.A., H. Aurich et al: "Oxidation of n-tetradecane-1-14C by a Cell Free Extract of *Acinetobacter calcoaceticus*", and Z. Allg. Mikrobiol., 1977, 17(3), 249–251, *Abstract*.
Chemical Abstracts, vol. 89, No. 21, Nov. 20, 1978, p. 228, No. 175496f, Columbus, Ohio, U.S.A., O. Asterger et al.: "Oxidation of Long-Chain n-alkanes by Cell—Free Extracts of *Acinetobacter calcoaceticus*. Identification and Determination of n-tetradecanoic Acid after Incubation with n-tetradecane", and Leipzig, Math-.-Naturwiss. Reihe 1978, 27(1), 3–15, *Abstract and Full Text*.
R. Whittenbury, et al., (J. Gen. Microbiol., 1970, 61, 205–218).
J. deBont, et al., (J. Gen. Microbiol., 1974, 83, 113–121).
J. F. Wilkinson ("Microbial Growth on $C_1$ Compounds," 1975, 45–57).
A. W. Thomson, et al., (Arch. Microbiol., 1976, 109, 243–246).
G. M. Tong, et al., (Biochem. J., 1977, 161, 333–344).
J. Colby, et al., (Biochem. J. 1977, 165, 395–402).
J. Colby, et al., (Biochem. J., 1977, 157, 495–497).
Higgins, et al., (Biochem. Biophys, Res. Comm., 89, 671).
D. I. Stirling, et al., (Eur. J. Biochem., 1979, 96, 205–212.
D. I. Stirling, et al., (FEMS Microbiology Letters, 5, 1979, 315–318).
W. R. Finnerty, et al., Z Allgem. Mikrobiol., 1962, 2, 1969.
Z. Zawadski, et al., Acta. Microbiol. Polon., 1979, 28, 315.
R. J. Neufeld, et al., Appln. Environ. Microbiol., 1970, 39, 511.
C Breuil, et al., Can. J. Microbiol., 1975, 21, 2103.
J. D. Walker, et al., Can. J. Microbiol., 1976, 22, 866.
M. A. Patrick, et al., J. Bact., 1974, 119, 76.
J. Le Petit, et al., Ann. Microbiol., (Paris), 1975, 126A, 367.

*Primary Examiner*—Ferris H. Lander
*Attorney, Agent, or Firm*—Cushman, Darby & Cushman

[57] ABSTRACT

A process of oxidizing a hydrocarbon which is an alkane or alkene or substituted alkane or alkene by contacting it with a culture of a bacterium as deposited under accession number NCIB 11613 or a mutant or derivative thereof which is capable of utilizing an alkane having from 6 to 28 carbon atoms as a source of carbon and energy or an enzyme extract thereof, and separating an oxidized derivative of the hydrocarbon.

7 Claims, No Drawings

MICROBIOLOGICAL OXIDATION PROCESS

This invention relates to a microbiological oxidation process for the oxidation of organic compounds and to novel micro-organisms useful as oxidising agents in such a process.

In recent years considerable attention has been paid to oxidations of organic compounds using bacteria which are capable of utilizing $C_1$-organic compounds as sources of carbon and energy. Such $C_1$-utilizing bacteria, for example strains of the species *Methylosinus trichosporium* and *Methylococcus capsulatus*, have been known for many years and cannot usually utilize more complex carbon sources such as ethane for growth. However it was found that such $C_1$-utilizing bacteria are capable of oxidizing a number of simple organic molecules such as ethane, propane, butane and ethene. These oxidations of simple organic molecules are discussed in papers by R Whittenbury et al (J. Gen. Microbiol., 1970, 61, 205–218), J A M de Bont et al (J. Gen. Microbiol., 1974, 83, 113–121), J F Wilkinson ("Microbial Growth on $C_1$ compounds", 1975, 45–57), A W Thomson et al (Arch. Microbiol., 1976, 109, 243 246) and G M Tonge et al (Biochem. J., 1977, 161, 333–344). More recently it has been found that the range of organic compounds which such $C_1$-utilizing bacteria are capable of oxidising is much larger than earlier workers had expected, including alkenes having from 3–8 carbon atoms, benzene and derivatives thereof, napthalene and derivatives thereof, heterocyclic compounds such as pyridine, cycloalkanes and longer chain alkanes having from 5 to 16 carbon atoms. This later work is described in published U.K. patent Specification Nos. 2,018,772A, 2,018,822A, 2,019,390A, 2,024,205A and 2,045,748A and in papers by J Colby et al (Biochem. J. 1977, 185, 395–402), Higgins et al (Biochem. Biophys, Res. Comm., 89, 671) and D I Stirling et al (Eur. J. Biochem., 1979, 96, 205–212 and FEMS Microbiology Letters, 5, 1979, 315–318).

The numerous oxidations which can be catalysed by $C_1$-utilizing micro-organisms include oxidations of longer chain alkanes, i.e. alkanes having from 6 to 28 carbon atoms, to corresponding alkanols. Many micro-organisms both yeasts and bacteria are known which are capable of utilizing alkanes having from 6 to 28 carbon atoms as sources of carbon and energy. Such micro-organisms include bacteria of the genus Acinetobacter (also known as *Micrococcus cerificans*) for example those reported in the following papers and patent specifications:

1. W R Finnerty et al, Z Allgem. Mikrobiol., 1962, 2, 169;
2. U.S. Pat. No. 3,634,194;
3. J P Kleber et al, Z Allgem. Mikrobiol, 1973, 13, 445;
4. Z Zawadzki et al, Acta. Microbiol. Polon. 1979, 28, 315;
5. R J Neufeld et al, Appl. Environ. Microbiol., 1980, 39, 511;
6. C Breuil et al, Can. J. Microbiol, 1975, 21, 2103;
7. J D Walker et al, Can. J. Microbiol., 1976, 22, 866;
8. M A Patrick et al, J. Bact., 1974, 119, 76;
9. J Le Petit et al., Ann. Microbiol. (Paris), 1975, 126A, 367.

According to the invention we provide a process for the oxidation of a hydrocarbon, which is an alkane or cycloalkane preferably having from 6 to 28 carbon atoms or an alkene having from 2 to 18 carbon atoms or a substituted alkane or alkene, wherein a culture of a bacterium belonging to the species of which NCIB 11613 is a member and capable of utilizing an alkane having from 6 to 28 carbon atoms as a source of carbon and energy, or an enzyme extract thereof is used as an oxidising agent, and recovering an oxidised derivative of the hydrocarbon. Preferably the bacterium is NCIB 11613 or a variant or mutant or derivative thereof.

Acinetobacter strain NCIB 11613 was isolated from mud from the estuary of the River Medway, Kent, England on Jan. 30, 1980 and screened for its ability to grow on crude oil from the North Sea Forties Field. Cultures of the micro-organism were deposited at the National Collection of Industrial Bacteria, Torrey Research Station, Aberdeen, Scotland, UK on Sept. 29, 1980.

The microbiological characteristics of Acinetobacter strain NCIB 11613 as determined by standard microbiological tests are as follows:

Microscopic morphology: Gram negative, coccoid rods, non-motile but with pili.

Colonial morphology: Entire and umbate, smooth and non-pigmented.

Physiological and Biochemical Tests

Catalase: +ve
Gram stain: −ve
Oxidase: −ve
glucose: does not produce acid or gas
Hugh and Liefson Test: −ve

Metabolism of carbon sources

Alkanes—chain length $C_7$–$C_{28}$: +ve
Alkan-1-ols—chain length $C_7$–$C_{16}$: +ve
Alkanaldehydes—chain length $C_7$–$C_{16}$: +ve
Succinic acid: +ve
Acetate: +ve
Ethanol: +ve
Benzoic acid: +ve
Glucose: −ve
Ribose: −ve
Galactose: −ve
Fructose: −ve
Benzene: −ve Acinetobacter strain NCIB 11613 contains a large plasmid which when removed by curing renders the strain auxotrophic for arginine.

Acinetobacter strain NCIB 11613 is a gram negative bacterium.

The oxidation process of the invention can be used to oxidase a wide range of alkanes and alkenes. It is however most useful for the oxidation of alkanes having from 6 to 28 carbon atoms and alkenes having from 2 to 18 carbon atoms, the products being the corresponding alkanols and the corresponding epoxides respectively. Alkanes which may be oxidised include both branched and straight-chain alkanes. Substituted alkanes may also be oxidised by the process of the invention. The invention is most usefully applied to the oxidation of n-alkanes and n-alkenes, particularly n-alkanes having from 6 to 16 carbon atoms and n-alkenes 2 to 14. The product of the oxidation of an n-alkane which is preferred is the corresponding alkan-1-ol. In cases where the oxidation proceeds further to produce e.g. alkanoic acids, biomass or $CO_2$, the further oxidation may be prevented or reduced by inclusion of appropriate inhibitors in the reaction mixture. Examples of specific alkanes which may be oxidised include hexane, heptane, octane, nonane, decane, tridecane, tetradecane and hexadecane. Alkenes which may be oxidised include straight and branched chain alkenes having terminal or internal double bonds and substituted alkenes. Preferably the oxidation is of straight chain alkenes, particularly those having from 2 to 18 carbon atoms. Oxidation occurs at the double bond.

The process of the invention is also applicable to the oxidation of cycloalkanes, for example cyclohexane, to cycloalkanols and substituted benzenes, having alkyl- or alkenyl-substituents containing up to 12 carbon atoms. The products obtained by the oxidation of cycloalkanes are cycloalkanols.

In a preferred medium inorganic nutrients are included as follows (concentrations are in g/l):
$(NH_4)_2SO_4$: 1.8
$MgSO_4.7H_2O$: 0.2
$NaH_2PO_4.2H_2O$: 1.56
$K_2HPO_4$: 1.9

To this medium is added (in proportions of 1 ml to 1 l of medium) a trace elements solution made up as follows (concentrations in mg/l):
$FeSO_4.7H_2O$: 500
$CuSO_4.5H_2O$: 100
$MnSO_4.5H_2O$: 50
$ZnSO_4.7H_2O$: 50
$CaCl_2.2H_2O$: 1320
$CoCl_2$: 10
$H_3BO_3$: 7
$Na_2MoO_4$: 10

The pH of the completed inorganic nutrients medium was adjusted to pH 6.8 with a suitable buffer.

Preferred conditions for growth are: pH 5.5–8, particularly 6.5–7.5: temperature 25° C.–37° C., particularly 28°–32° C.

When required for the oxidation process of the invention, bacteria may be transferred from the medium used for their growth into a medium which lacks a nitrogen source and is therefore a medium in which they cannot grow, or the oxidation may be carried out during the growth stage. Particularly suitable as this non-growth medium is an aqueous medium buffered with phosphate to pH 7. The compound to be oxidised may be supplied to a reactor containing the bacteria in the non-growth medium and the oxidation process can be performed preferably at a temperature in the range 25°–37° C. The bacteria are preferably maintained in the absence of nitrogen for periods up to 2 days, after which time they may be either returned to the growth medium for renewed cultivation or discarded. Suitably the oxidation reaction is carried out in presence of oxygen supplied for example as air.

The oxidation process of the invention may be performed using whole bacterial cells or suitable enzyme extracts derived from these cells, e.g. extracts containing alkane hydroxylases. The enzyme extracts may be prepared by mechanically breaking down the microorganisms, discarding any supernatant liquid and using the remaining cell membrane material, together with a suitable source of NADH, in the oxidation process.

The invention is illustrated by the following examples:

EXAMPLE 1

Cells of Acinetobacter strain NCIB 11613 were grown at 30° C. in a medium as described on page 6 lines 5 to 23 containing 1% by volume dodecane as the sole carbon and energy source. The cells were harvested by centrifugation and resuspended in 30 mM. of an aqueous solution containing 1.56 g/l of $NaH_2PO_4.2H_2O$ and 1.9 g/l of $K_2HPO_4$ as a buffer, of pH 7.0, to give a cell dry weight of 2.3 gm/l.

In a series of experiments 25 ml aliquots of this suspension were shaken with 5 ml. of each of the hydrocarbons listed below in the Table at 30° C. After 21 hours in each experiment, a sample of hydrocarbon phase was separated and analysed for products by gas/liquid chromatography. The results are set out in the following Table:

TABLE

| Alkane used | Product Measured | Amount of product (mg) |
| --- | --- | --- |
| n-octane | n-octan-l-ol | 37.8 |
| n-decane | n-decan-l-ol | 10.5 |
| n-dodecane | n-dodecan-l-ol | 1.2 |
| n-tetradecane | n-tetrandecan-l-ol | 0.4 |
| n-hexadecane | n-hexadecan-l-ol | 0.2 |
| n-dodec-l-ene | n-dodec-l-ene epoxide | 1.0 |

EXAMPLE 2

25 mls of a cell suspension of NCIB 11613 prepared as in Example 1 was shaken with cyclohexane in a centre well. After 21 hours, the cell suspension was extracted with ether, and the extract separated and analysed for products by gas/liquid chromatography. It was found that 1.0 mg of cyclohexanol had been produced.

EXAMPLE 3

Example of Use of Cured Strain for Alkane Oxidation

A cured strain (NCIB 11728) of Acinetobacter strain NCIB 11613 was produced by exposing it to sublethal doses of acridine orange (50 μg/ml). The cured strain will not grow on simple mineral salts media containing hydrocarbons or acetic or succinic acids as sole sources of carbon and energy, but will grow on these substrates in the presence of 40 μg/ml of arginine. Gel electrophoresis of cell extracts shows that a plasmid of molecular weight $70 \times 10^6$, present in the wild type, is absent in the cured strain.

The cured strain was inoculated into 250 ml of a nutrient medium prepared as in Example 1 but containing in addition 40 μg/ml of arginine and 2.5 ml of n-dodecane, contained in a 1 l baffled conical flask. The cells were grown by agitating the flask on a rotary shaker at 30° C. for 18 hours. A sample of the alkane phase was then allowed to separate. Dodecan-1-ol was separated from the alkane phase (0.05% w/w) by gas-liquid chromatography.

I claim:

1. A process of oxidising a hydrocarbon which is an alkane or alkene or substituted alkane or alkene by contacting it with a culture of a bacterium as deposited under accession number NCIB 11613 or a mutant or derivative thereof which is capable of utilising an alkane having from 6 to 28 carbon atoms as a source of carbon and energy or an enzyme extract thereof, and separating an oxidised derivative of the hydrocarbon.

2. A process as claimed in claim 1 in which an alkane having 6 to 28 carbon atoms is oxidised to the corresponding alkanol.

3. A process as claimed in claim 2 in which the alkane is a normal alkane having 8 to 14 carbon atoms.

4. A process as claimed in claim 1 in which a cyclic alkane is oxidised to the corresponding alkanol.

5. A process as claimed in claim 1 in which bacteria are transferred from the medium used for their growth into a medium which lacks a nitrogen source and the compound to be oxidised is contacted with the bacteria in this medium.

6. A process as claimed in claim 5 in which the compound to be oxidised is contacted with the bacteria at a temperature in the range 25° to 37° C. and in the presence of oxygen.

7. A process as claimed in claim 1 in which an alkene is oxidised to an epoxide.

* * * * *